US012613211B2

(12) United States Patent
Ileleji et al.

(10) Patent No.: US 12,613,211 B2
(45) Date of Patent: Apr. 28, 2026

(54) GRAIN MOISTURE METER NETWORKED TO SMARTPHONES

(71) Applicants:Purdue Research Foundation, West Lafayette, IN (US); Universidad de los Andes, Bogotá (CO)

(72) Inventors: Klein Erhekabor Ileleji, Carmel, IN (US); Alba Graciela Avila Bernal, Bogota (CO); Marisol Pantoja Otero, Berkely, MI (US)

(73) Assignee: Purdue Research Foundation, West Lafayette, IN (US)

( * ) Notice: Subject to any disclaimer, the term of this patent is extended or adjusted under 35 U.S.C. 154(b) by 322 days.

(21) Appl. No.: 18/547,166

(22) PCT Filed: Feb. 22, 2022

(86) PCT No.: PCT/US2022/017337
§ 371 (c)(1),
(2) Date: Aug. 21, 2023

(87) PCT Pub. No.: WO2022/182666
PCT Pub. Date: Sep. 1, 2022

(65) Prior Publication Data
US 2024/0133836 A1 Apr. 25, 2024
US 2024/0230573 A9 Jul. 11, 2024

Related U.S. Application Data

(60) Provisional application No. 63/152,384, filed on Feb. 23, 2021.

(51) Int. Cl.
*G01N 27/22* (2006.01)
*G01N 33/10* (2006.01)

(52) U.S. Cl.
CPC ........... *G01N 27/223* (2013.01); *G01N 33/10* (2013.01)

(58) Field of Classification Search
CPC ....... G01N 27/223; G01N 33/10; G01D 21/00
USPC ......................... 324/664, 663, 658, 649, 600
See application file for complete search history.

(56) References Cited

U.S. PATENT DOCUMENTS

| | | | | |
|---|---|---|---|---|
| 6,917,206 B2 * | 7/2005 | Rains | .................. | A01D 41/1277 |
| | | | | 324/667 |
| 11,309,669 B2 * | 4/2022 | Whipple | ............ | H01H 71/0207 |
| 11,360,149 B2 * | 6/2022 | Haddej | ................ | G01R 31/367 |
| 11,875,623 B2 * | 1/2024 | Andersen | ........... | G07C 9/00896 |
| 2010/0277185 A1 * | 11/2010 | Hughes | ................ | G01N 33/246 |
| | | | | 324/664 |
| 2024/0402117 A1 * | 12/2024 | Beck | .................... | G01N 27/223 |

* cited by examiner

*Primary Examiner* — Giovanni Astacio-Oquendo
(74) *Attorney, Agent, or Firm* — Kevin R. Erdman; Brannon Sowers & Cracraft PC

(57) ABSTRACT

An assembly (decoupled grain sampler and moisture content reader) for measuring grain moisture and sharing the grain moisture information with a database, other framers, and merchants, including a grain receiving chamber, at least one plate capacitor operationally connected to the grain receiving chamber, a capacitance to digital converter (or similar device) operationally connected to the at least one plate capacitor, a microprocessor operationally connected to the oscillator, a user interface operationally connected to the microprocessor, a smartphone app in operational communication with the microprocessor, and a transceiver operationally connected to the microprocessor and the smartphone app.

12 Claims, 6 Drawing Sheets

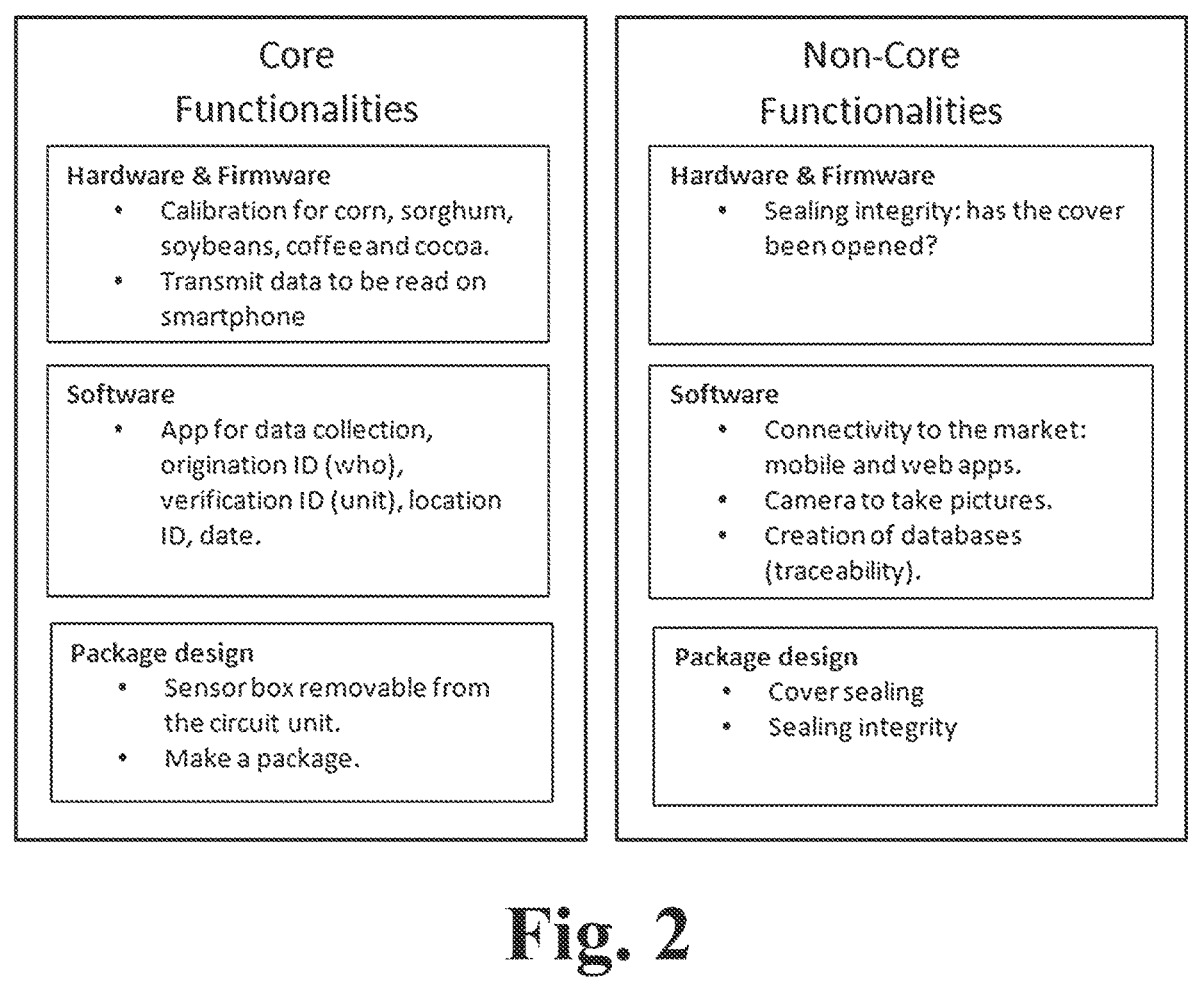

Core Functionalities

Hardware & Firmware
- Calibration for corn, sorghum, soybeans, coffee and cocoa.
- Transmit data to be read on smartphone

Software
- App for data collection, origination ID (who), verification ID (unit), location ID, date.

Package design
- Sensor box removable from the circuit unit.
- Make a package.

Non-Core Functionalities

Hardware & Firmware
- Sealing integrity: has the cover been opened?

Software
- Connectivity to the market: mobile and web apps.
- Camera to take pictures.
- Creation of databases (traceability).

Package design
- Cover sealing
- Sealing integrity

Fig. 2

| ID | Frequency (kHz) | | | Average [kHz] |
|---|---|---|---|---|
| | 1 | 2 | 3 | |
| 1.1 | 47.27 | 48.13 | 47.84 | |
| 1.2 | 47.28 | 48.12 | 47.85 | |
| 1.3 | 47.26 | 48.11 | 47.83 | |
| AVERAGE | 47.27 | 48.12 | 47.84 | 47.74333 |
| 2.1 | 44.25 | 44.08 | 44.65 | |
| 2.2 | 44.18 | 44.05 | 44.63 | |
| 2.3 | 44.15 | 44.02 | 44.62 | |
| AVERAGE | 44.19333 | 44.05 | 44.63333 | 44.29222 |
| 3.1 | 36.96 | 36.36 | 36.57 | |
| 3.2 | 36.97 | 36.36 | 36.58 | |
| 3.3 | 36.97 | 36.36 | 36.57 | |
| AVERAGE | 36.96667 | 36.36 | 36.57333 | 36.63333 |
| 4.1 | 35.24 | 33.8 | 35.78 | |
| 4.2 | 35.11 | 33.72 | 35.69 | |
| 4.3 | 35.01 | 33.7 | 35.62 | |
| AVERAGE | 35.12 | 33.74 | 35.69667 | 34.85222 |
| 5.1 | 31.88 | 31.75 | 32.4 | |
| 5.2 | 31.66 | 31.59 | 32.27 | 31.84667 |
| 5.3 | 31.46 | 31.46 | 32.15 | |
| AVERAGE | 31.66667 | 31.6 | 32.27333 | |
| 6.1 | | 30.44 | 29.39 | |
| 6.2 | | 30.26 | 29.11 | |
| 6.3 | | 30.10 | 28.92 | |
| AVERAGE | | 30.27 | 29.14 | 29.70333 |
| 7.1 | 25.4 | 24.21 | 25.17 | |
| 7.2 | 25.31 | 24.18 | 25.12 | |
| 7.3 | 25.18 | 24.15 | 25.08 | |
| AVERAGE | 25.29667 | 24.18 | 25.12333 | 24.86667 |
| 8.1 | 47.27 | 26.88 | 26.94 | |
| 8.2 | 47.28 | 26.87 | 26.89 | |
| 8.3 | 47.26 | 26.85 | 26.86 | |
| AVERAGE | 47.27 | 26.86667 | 26.89667 | 33.67778 |

Fig. 7

GRAIN MOISTURE METER NETWORKED TO SMARTPHONES

CROSS-REFERENCE TO RELATED APPLICATIONS

This patent application claims priority to co-pending U.S. provisional patent application Ser. No. 63/152,384, filed on Feb. 23, 2021.

TECHNICAL FIELD

This disclosure relates generally to agriculture, and, more specifically, to a method and apparatus for automatically and remotely measuring and monitoring moisture in grains.

BACKGROUND

This section introduces aspects that may help facilitate a better understanding of the disclosure. Accordingly, these statements are to be read in this light and are not to be understood as admissions about what is or is not prior art.

Moisture content of grains and oilseeds is a significant factor in food quality and moisture content has emerged as one of the quality indices for grains. Moisture content is related to food safety requirements and thus the value of the commodity. While farmers who use mechanized and advance crop production methods in developed countries such as those in North America, Europe, and the like use digital moisture meters to measure the moisture content of grains and oilseeds, farmers in developing countries still measure moisture using subjective methods (biting, feeling by hand, sound by shaking, and the like). Subjective methods require a great deal of experience to be accurate and have been found to inconsistent even for experienced farmers.

Moisture content is one of the most important attributes of crop quality. However, this attribute is NOT objectively measured in most parts of the developing world due to limited access to moisture meters, which are prohibitively expensive. Most importantly, most farmers are effectively excluded from quite lucrative markets because of their inability to meet market standards due to lack of ability to accurately measure and document produce quality. Additionally, grains are at risk of getting spoiled when their moisture content is not known.

Currently, portable hand-held moisture sensors in the market manufactured by well-known companies are too expensive (about $300) and beyond the reach of small and medium holder farmers in developing countries. Additionally, none of these moisture meters have the means to capture data to share between remote trading partners for transaction purposes. On these devices, data is still captured via an LCD display and transcribed to paper by hand, making the data prone to manipulation and hard to track, which poses a major problem for long-distance trade transactions between the seller and buyer. Also, most of these units couple both the sample cup and meter readout together, making it necessary to acquire a device with two separate entities in one, which while convenient is expensive to make the moisture meter work for the end-user. Additionally, most moisture meters in the market today do not tag the location where the moisture content was measured, which is quite important in traceability analysis or for field scouting purposes.

Thus, there exists an unmet need for cost-effective measurement of grain moisture and data manipulation and improved connectivity of the farmer with the market. The present novel technology addresses this need.

BRIEF DESCRIPTION OF THE DRAWINGS

FIG. 2 is a graphical presentation of core and non-core functionalities of the device of FIG. 1.

FIG. 7 schematically illustrates the firmware of the circuit interface and data capture functions of the device of FIG. 1.

DETAILED DESCRIPTION

Figure 1:
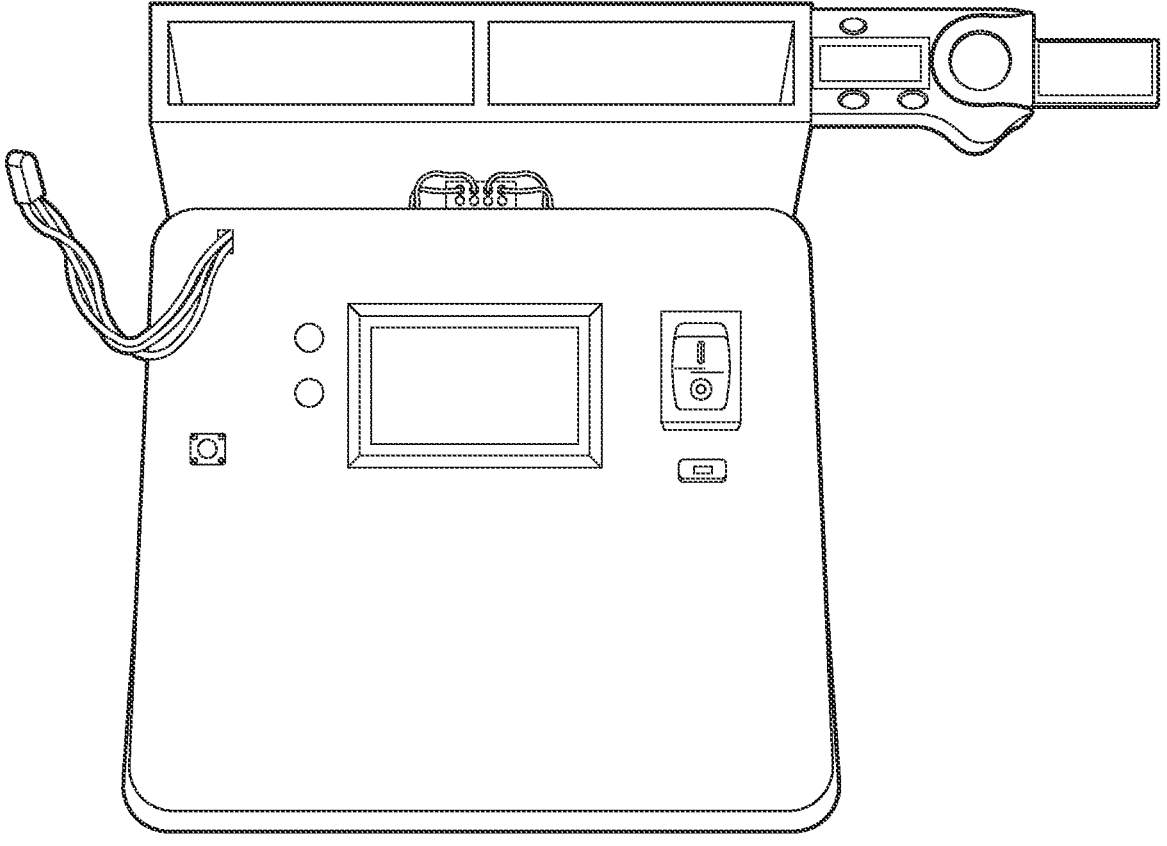
FIG. 1 is a perspective view of a moisture measurement device according to a first embodiment of the present invention.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended.

Currently, the moisture meters for grains available in the market are expensive, do not have wireless data communication, lack data storage capacity, display data solely on LCD or like screens, and have their sensing box attached to the main body of the meter. These meters are fabricated by well-known companies and have a good accuracy and may be calibrated for up to 20 crops, but for many farmers it is not possible to afford a 300 USD moisture meter. The users of these units must personally take notes of the values displayed by the meter, which give rise to honest error as well as dishonest data manipulation. Some of the units enable the connection of a cable to a PC using an RS-232 port for data capture. This connectivity to systems such as a PC of course requires a PC, which is beyond the reach of most small and medium-holder farmers. Additionally, these moisture meters do not take into account applications for crop scouting purposes.

Recently, other more affordable means of measuring moisture content that have been developed. These systems include a relatively inexpensive grain probe developed by Dr. Paul Armstrong of the USDA-ARS lab in Manhattan, KS, and methods that use the moisture sorption isotherm for grain to predict whether the grain has been sufficiently dried prior to storage However, these methods enjoy limited use by farmers making decisions about whether the grain is dried enough for storage and are not enabled to link farmers with grain traders or financial institutions.

Additionally, when taking measurements, the fact that the sensor array is attached to the meter restricts the true verification of the sample, because there is no guarantee that the sample measured is the same after it has been disposed from the sampler. Furthermore, the individual making the moisture measurements in developing countries is not usually the farmer, but grain aggregators whose interests are not necessarily aligned with those of the farmers. The smart sampling case of the instant novel technology decouples the crop (grain) sampler from the reader and allows rapid reading of sampling cups from a single reader. Farmers could own the sampling cups while the grain merchants own the reader, or readers could be shared between farmers, making the overall system affordable to smallholder farmers.

In case of foodborne disease outbreaks, local public health and regulatory officials partner with the farming industry and spend a lot of resources to perform investigations. This process includes the analysis of large amounts of information containing traceback data as one of the sources. In the US, there are web-based applications which require close collaboration, communication, and data sharing among local, state, and federal health and regulatory officials. Yet, these measurements do not have direct input from the farmers about moisture contents, and this application is not present at all in developing countries.

Further, farmers do not have direct contact with the market, giving rise to miscommunication about quality and prices and leaving farmers without proof of the quality of their commodity, which is problematic when negotiating sales price and when trying to back bank loans.

Figure 3:
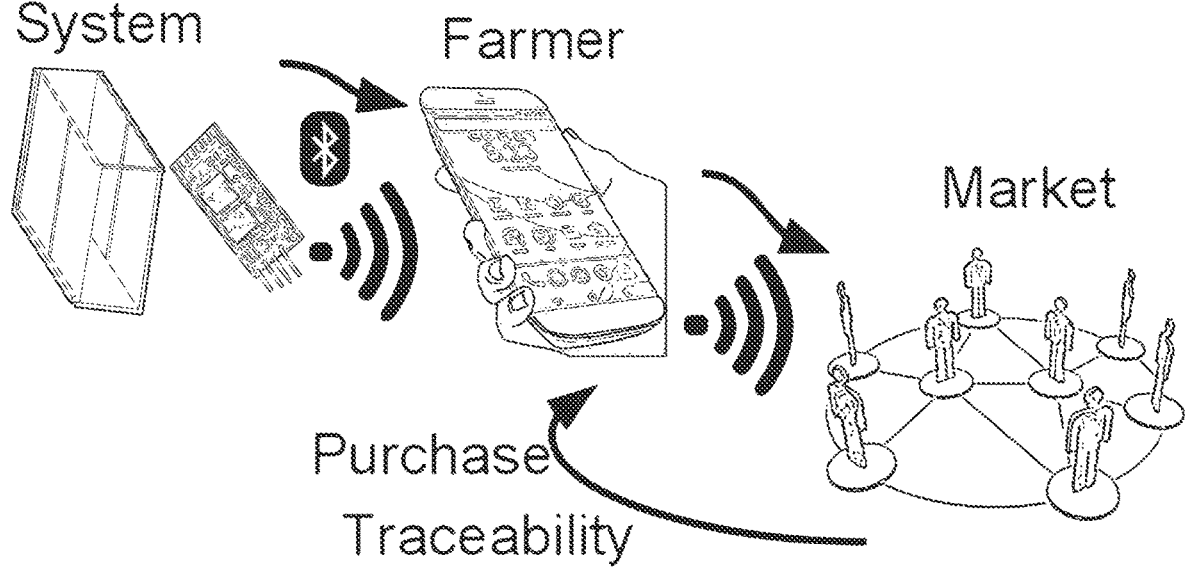
FIG. 3 is a schematic representation of a moisture measurement system using the device of FIG. 1.
Figure 4:
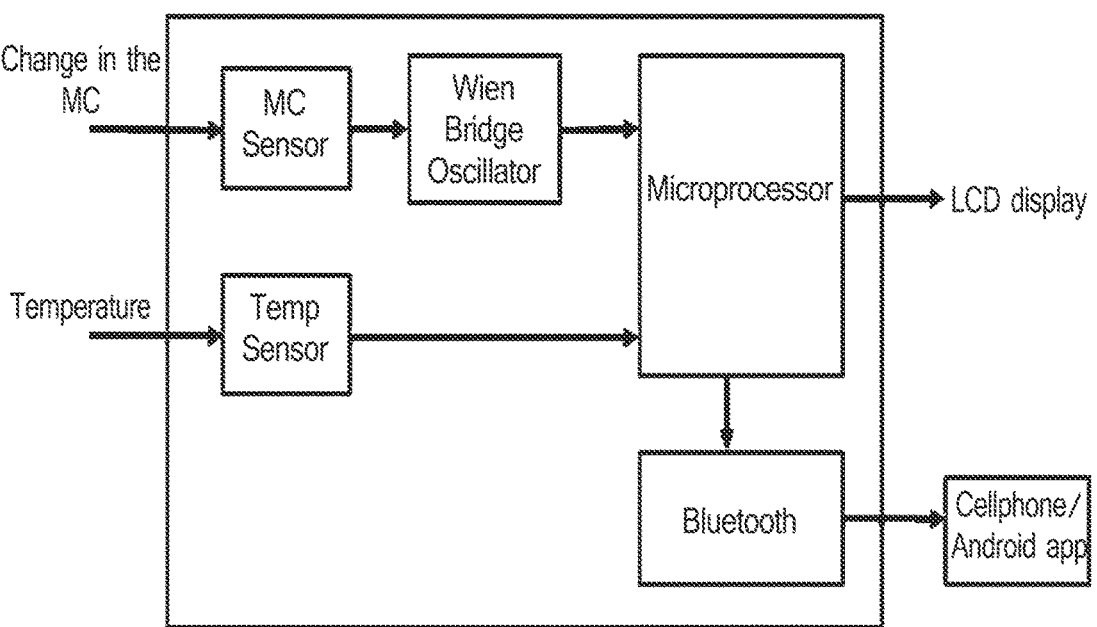
FIG. 4 is a schematic illustration of the device of FIG. 1.
Figure 5:
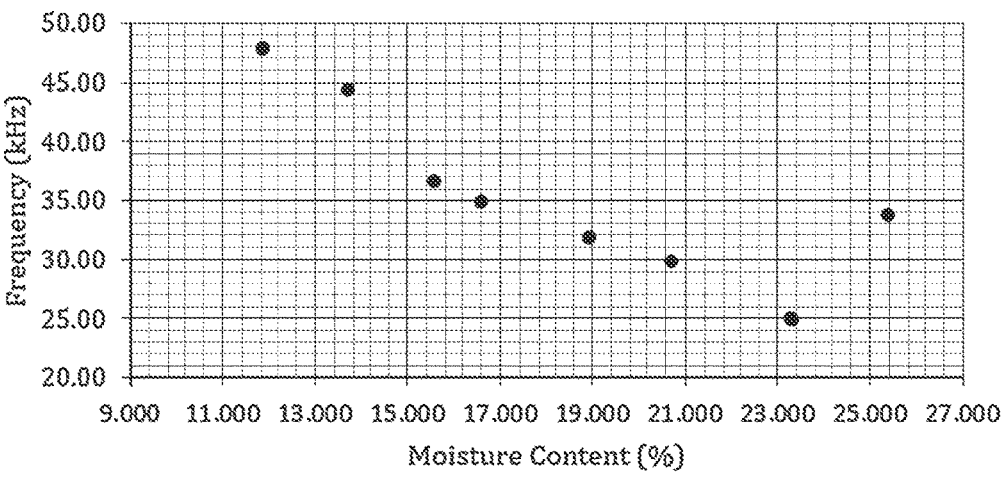
FIG. 5 is a perspective view of first and second grain receiving chambers with respective spaced plate capacitors disposed therein, as decoupled from the device of claim 1.
Figure 6:
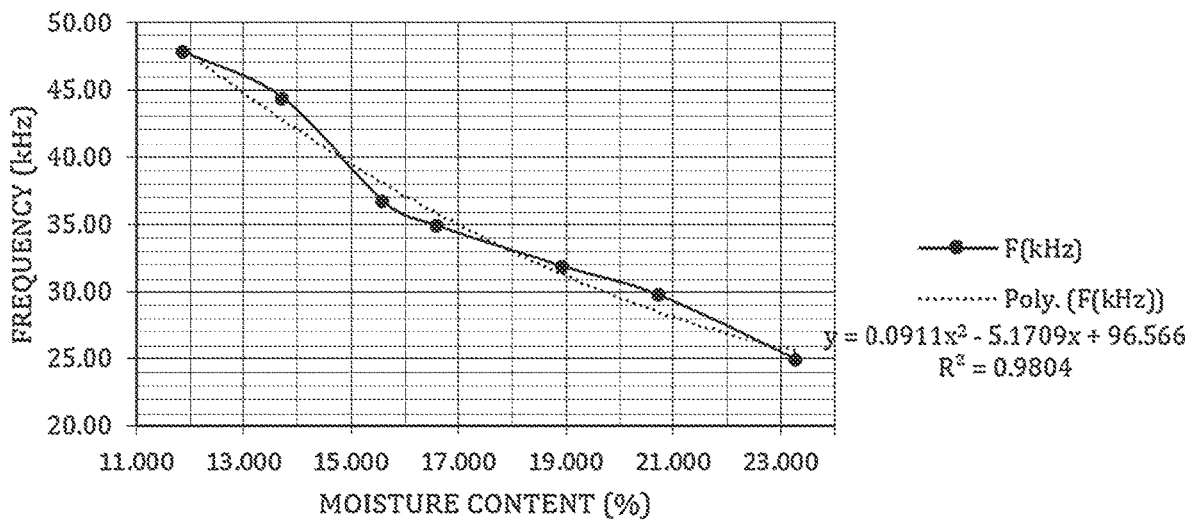
FIG. 6 is a perspective view of the device of FIG. 1 laden with grain.
Figure 8:
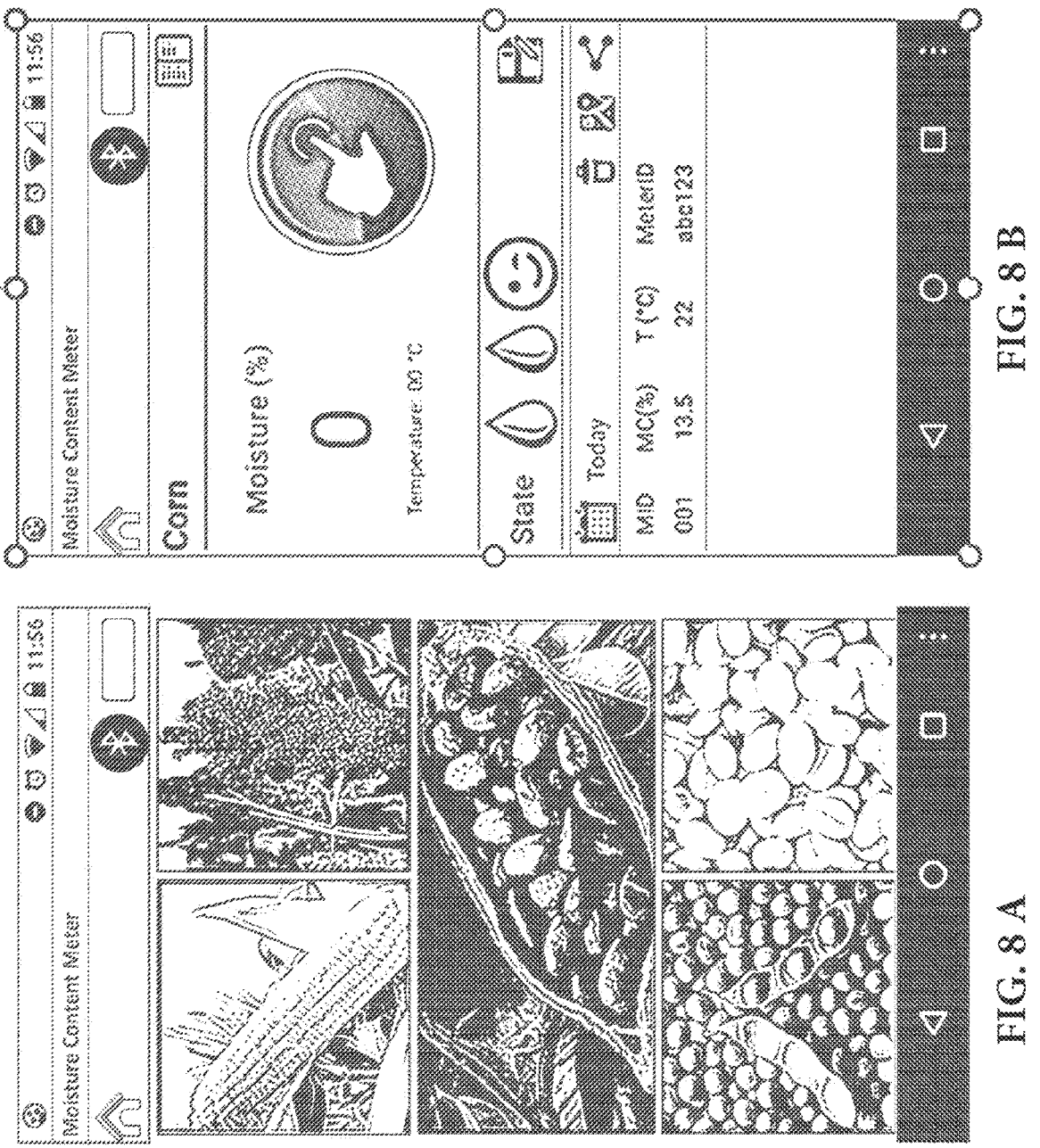
FIGS. 8A and 8B graphically illustrate a cell phone app user interface for the system of FIG. 3.

As illustrated in FIGS. 1-8B, the instant invention relates to a grain moisture assembly or system 100 with the ability to capture moisture data both on a device display (such as an LCD panel) and by logging using a smartphone via wireless connectivity such as Bluetooth or other similar means. The assembly 100 includes a moisture meter sensor device 105, a cellphone app 110 configured to communicate with the device 105, and a database 115 in communication with the device 105 and/or the app 110.

The moisture sensing device 105 includes a grain receiving module 120 operationally connected to a processing module 125.

Referring to FIG. 2, the grain receiving module 120 includes first and second spaced grain receiving chambers 130, 135 with a dielectric wall 140 positioned therebetween. At least one moisture sensor 170 is positioned to detect the moisture content of grain disposed in each respective chamber 130, 135. In some embodiments, the moisture sensor 170 includes an oscillator 150 operationally connected to at least one pair of spaced capacitors 145, each respective pair of capacitors 145 disposed in a respective chamber 130, 135. A capacitance to digital converter 147 is operationally connected to each respective pair of spaced capacitors 145. A display 155 may likewise operationally connected to the oscillator 150.

The processing module 125 includes a microprocessor 160, a transceiver 165 operationally connected to the microprocessor 160, the at least one moisture sensor 170 operationally connected to the microprocessor 160, and at least one temperature sensor 175 for measuring the temperature of the grain disposed in each respective chamber 130, 135 and operationally connected to the microprocessor 160. The sensors 170, 175 are typically positioned to query one or both of the chambers 130, 135. The microprocessor 160 is operationally connected to the capacitance to digital converter 147, if one is present.

The cellphone app 110 is typically run on a cellphone 180 in the possession of the farmer using the system 100. The cellphone app 110 is configured to communicate with and/or establish a database 190. The database 190 may be hosted on a particular remote server, or may be cloud-based. The cellphone app 110 also generates a display interface 195 on the cellphone. One or more cellphone apps 110 may simultaneously query and communicate with the database 190, allowing for a networking of the cellphone apps 110.

One point of novelty is to use the networking platforms of smartphones 180 for moisture and other data sharing between the farmers (growers) and crop merchants (aggregators), crop sellers and buyers, crop commodity boards and financial institutions, enabling smallholder farmers to participate in more lucrative markets of the value chain. The grain moisture measurement unit 105 also decouples the moisture meter/sensor 170 from the sampling cup 120, enabling the secured transfer to samples in sampling cups 120 from one location to another, while maintaining its integrity from adulteration or manipulation. The instant moisture measurement system 100 empowers small- and medium-holder farmers with the means to directly market their crops to higher value markets in order to capture favorable prices rather than leave the margins of trade to a middleman. Additionally, the decoupling of the sampling cup 120 from the meter 125 would allow for secured rapid throughput screening, or sample verification between two distant parties should a dispute occur between parties. The data connectivity via smartphones 180 enable product traceability along the value-chain.

The moisture meter 105 is based on an inexpensive capacitive sensing technology that makes the device affordable. The moisture measurement system 100 measures both temperature and moisture content, and transmits the data by wireless communication via Bluetooth to an android or like device, where the data can be stored or shared. This data, plus the data that a smartphone can capture, enables the creation of a data base with information relevant to the activity: ID of the meter, of the farmer and of the smartphone, location of measurement, date, picture of the sample, and trading information.

The moisture meter 105 can be used for moisture determination of crops such as but not limited to, corn, sorghum, soybean, cocoa and coffee. Moreover, the system 100 incudes other core functionalities and data analytic tools that would have value to farmers, commodity buyers, processors, financial institutions and other agencies.

The solution provided by the novel meter 105 involves different actors from farmers to industries and government who are seeking data to make decisions. The interaction of the farmer with the moisture meter 105 and his phone 180 allows a completely new process of data sharing that will connect the farmer with the market for grain purchases and at the same time will generate traceable data, important for government and industries.

FIG. 2 shows the moisture meter systems design. The inputs of the system are the change of moisture content (MC) in the grain, the change in temperature and the push buttons used to adjust the bias of the calibration and navigation of the interface. The changes in MC and temperature are detected by the MC sensor and temperature sensor, respectively. The temperature sensor has an analog output that enters directly to the microcontroller, which has analog-to-digital conversion (ADC) capabilities. The moisture sensor output passes through the CDC FDC1004 where the change in capacitance is detected, converted into a digital signal, and sent to the microcontroller by I2C communication. The microcontroller gets the digital or analog signals from the sensors, processes them, computes the moisture content based on the calibration curves saved in the memory, and checks for battery power level. Finally, the microcontroller operates the interface components such as the LCD screen, the battery power-level LEDs and the navigation push buttons. The data is printed on the LCD or in the serial port to be either displayed or sent through Bluetooth to the Android app.

In one embodiment, the system 100 is used to conduct moisture determination for these selected crops: corn, sorghum, soybean, cocoa and coffee. However, other examples might include other core functionalities and data analytic tools that would have value to farmers, commodity buyers, processors, financial institutions and other agencies.

In one embodiment, the sensor 170 has guard electrodes to avoid fringing effect on the measurements and the box 120 has a new division 140 in the middle that creates two chambers 130, 135, in order to decrease the bulk density variations of the grain. The following diagrams further explain the system 100.

As shown in FIG. 7, the microcontroller 160 as programmed is based on two loops to manage navigation, the outer loop and the measurement inner loop. The system 100 checks and informs the battery voltage during initialization. The system 100 then allows the user to select the crop type and instructs the user to plug the filled sensor 120 to the circuit box 125. Then data can be captured and displayed, and subsequently data sent to the database 115, and the user can make several measurements in the inner loop such as via a "short press" of the "Enter" button. A "long press" of the "Enter" button may take the user out to the calibration state, which later allows the user to move onto the Crop state and select a new crop.

The cell phone (typically android) app 110 is the mechanism used to acquire grain quality (moisture content, etc.) data of the commodity, which is linked to farmer demographics that enables the creation of a global information systems for several purposes. The design requirements of the mobile app were inspired based on the connection to the market and traceability concepts. A graphic display of the quality condition of the commodity in terms of moisture content was designed, so farmers that do not know how to read the alphabet or understand numeric scales such as percentage moisture content could understand the meaning of the results. The app 110 was designed to collect data of moisture content, temperature, date, time, geographical coordinates, farmer ID and meter ID. The interface typically may enable data sharing and geographical visualization capabilities.

A smart phone application (app) 110 for a phone 180, or other electronic device, such as, but not limited to, Android and iPhone devices and the like, is described. The app 110 receives the wireless collection of various crop properties, such as moisture content and temperature measurements, taken by the meter unit 105. The app 110 allows the farmer to select the crop they desire to measure, collect the data, store the data, and share the data. This allows the creation and storing of a database, or records thereof, with information relevant to the activity: such as, for example, ID of the meter, of the farmer and of the smartphone, location of measurement, date, picture of the sample, and trading information. Depending on the range defined for the crop, the app will show to the farmer if the grain is good to store or if it needs more time to dry. This feature may be presented as number of water drops, and, in some cases, as an emoticon, or other indication, expressing whether the grain has reached a desirable level of dryness. A history of the information collected will be displayed, to allow the farmer, or other user, to keep track of the quality of its commodity. A non-limiting example is shown in FIGS. 8A and 8B.

It should be appreciated that communications with smart phones and other similar devices combines sensing, computation, information extraction, and communication functionalities together in one device, and may function similarly with other sensors and/or devices.

It should be recognized that the technology and methods and apparatuses of this disclosure addresses several issues facing the agricultural industry such as, but not limited to, postharvest loses due to lack of moisture content measurement; data manipulation; connectivity of the farmer with the market; data traceability to link foodborne disease outbreaks to a contaminated source absence of data that supports the value of the farmer's commodity when applying for bank loans or verification in a warehouse receipt system. The technology of this disclosure also provides a link between farmers and the market with regards to crop quality (moisture content) verification and transmission for transaction purposes, linking farmers to high-value markets or financial systems to secure loans.

In operation, a farmer using the moisture sensor apparatus 105 first loads a predetermined quantity of grain into a chamber 120, 130, 135. The predetermined amount of grain is then queried with an oscillator 150, such as a Wein bridge oscillator, operationally connected to at least on plate capacitor 145. The moisture sensor device 105 then calculates the moisture content of the predetermined amount of grain, and shares information regarding the moisture content of the predetermined amount of grain with a smartphone 180. A database 190 is established, and the smartphone 180 writes information to the database 190, including at least one of a meter ID, smartphone information, a location of measurement, data, pictures, and trading information.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

The invention claimed is:

1. A moisture sensor for grains, comprising:
a pair of grain chambers separated by a dielectric wall;
respective pairs of parallel disposed plate capacitors electrically connected in series and operationally connected to each respective grain chamber;
an oscillator operationally connected to each respective pair of parallel disposed plate capacitors;
an electronic controller operationally connected to the oscillator;
an IO interface operationally connected to the electronic controller; and
a smartphone app operationally connected to the electronic controller.

2. The moisture sensor of claim 1 further comprising a capacitance to digital converter operationally connected to the pair of parallel disposed plate capacitors for grain moisture measurement.

3. A smartphone application, comprising:
an app operational on a smartphone device;
the app configured to receive a wireless collection of various crop properties, including a moisture content from a meter unit, the moisture meter having an oscillator operationally connected to each of a respective pair of parallel disposed plate capacitors; an electronic controller operationally connected to the oscillator; and an interface operationally connected to the electronic controller in communication with the app;

the app facilitating selection of a crop, collection of data regarding the crop, storing data regarding the crop, and sharing data regarding the crop observed by and received from the moisture meter.

4. The smartphone application of claim 3, further including a database storing information including at least one of a meter ID, farmer ID, smartphone information, a location of measurement, grain moisture data, grain measurement date and time, measurement temperature data, pictures, and trading information.

5. A method of using a moisture sensor, comprising:

loading a predetermined amount of grain into a chamber;

querying the predetermined amount of grain with an oscillator operationally connected to at least one plate capacitor, wherein the oscillator is operationally connected to at least one plate capacitor of a pair of parallel disposed plate capacitors; and wherein an electronic controller is operationally connected to the oscillator and has an interface operationally connected to the electronic controller, and wherein a smartphone app is operationally connected to the electronic controller;

calculating the moisture content of the predetermined amount of grain with the electronic controller; and sharing the moisture content of the predetermined amount of grain with a smartphone via the smartphone app.

6. The method of claim 5 further comprising:

establishing a database storing information including at least one of a meter ID, smartphone information, a location of measurement, data, pictures, and trading information.

7. A moisture sensor assembly for measuring the moisture content of grains, comprising:

at least one grain receiving chamber;

a moisture sensor operationally connected to the at least one grain receiving chamber, the moisture sensor having an oscillator operationally connected to each of a respective pair of parallel disposed plate capacitors; an electronic controller operationally connected to the oscillator; an interface operationally connected to the electronic controller; and a smartphone app operationally connected to the electronic controller;

a microprocessor operationally connected to the at least one moisture sensor;

a user interface operationally connected to the microprocessor;

a smartphone app in operational communication with the microprocessor; and a transceiver operationally connected to the microprocessor and the smartphone app.

8. The moisture sensor assembly for measuring the moisture content of grains of claim 7 wherein the moisture sensor further comprises a pair of spaced plate capacitors disposed within the at least one grain receiving chamber and an oscillator operationally connected to the par of spaced plate capacitors; wherein the microprocessor is operationally connected to the pair of spaced plate capacitors and to the oscillator.

9. The moisture sensor assembly for measuring the moisture content of grains of claim 7 further comprising a database operationally connected to the smartphone app.

10. The moisture sensor assembly for measuring the moisture content of grains of claim 9 wherein the database is cloud-based.

11. The moisture sensor assembly for measuring the moisture content of grains of claim 7 wherein the grain receiving chamber includes a first and a second sub-chamber and a dielectric wall disposed between the first and second sub-chambers.

12. The moisture sensor assembly for measuring the moisture content of grains of claim 7 further comprising a temperature sensor operationally connected to the microprocessor and positioned to measure the temperature in the grain receiving chamber.

* * * * *